United States Patent [19]
Bailey et al.

[11] Patent Number: 5,620,442
[45] Date of Patent: Apr. 15, 1997

[54] METHOD AND APPARATUS FOR EXTERNAL FIXATION OF SMALL BONES

[76] Inventors: Kirk J. Bailey, 7 Crescent South, Andover, N.J. 07821; Sean P. Curry, 927 Castle Point Ter., Hoboken, N.J. 07030; John S. Mahaffey, 57 Duck Hawk Ct., Hackettstown, N.J. 07840

[21] Appl. No.: 439,696

[22] Filed: May 12, 1995

[51] Int. Cl.⁶ ...................................................... A61B 17/56
[52] U.S. Cl. ................................................ 606/54; 606/57
[58] Field of Search ................................ 606/53–59, 60, 606/61

[56] References Cited

U.S. PATENT DOCUMENTS

| 1,869,726 | 8/1932 | Youngren . |
| 1,997,466 | 4/1935 | Longfellow . |
| 2,020,262 | 11/1935 | Longfellow . |
| 2,055,024 | 9/1936 | Bittner, Jr. . |
| 2,238,870 | 4/1941 | Haynes . |
| 2,250,417 | 7/1941 | Ettinger . |
| 2,251,209 | 7/1941 | Stader . |
| 2,333,033 | 10/1943 | Mraz . |
| 2,346,346 | 4/1944 | Anderson . |
| 2,391,537 | 12/1945 | Anderson . |
| 3,547,113 | 12/1970 | Swanson .................................. 128/84 |

FOREIGN PATENT DOCUMENTS

| 203544 | 6/1939 | France . |
| 2213283 | 8/1973 | Germany . |
| 448010 | 10/1974 | U.S.S.R. . |

OTHER PUBLICATIONS

EBI Medical Systems brochure, "New Ball Joint Articulating Ankle", 1 page, dated Jul., 1994.
EBI Medical Systems brochure, "If You Think Orthofix Is Just for Fractures . . . Think Again!", 1 page, dated Jan., 1994.
Biomet, Inc. brochure entitled "Hammer External Fixation Systems", 1 double–sided page, copyright 1994.
Biomet, Inc. brochure entitled "Hammer Mini–Tubular External Fixation Surgical Technique", 9 pp., undated.

*Primary Examiner*—Michael Powell Buiz
*Assistant Examiner*—Mark S. Leonardo
*Attorney, Agent, or Firm*—Harness, Dickey & Pierce, P.L.C.

[57] ABSTRACT

An external fixator for securing a first bone portion in a fixed relationship with respect to a second bone portion. The fixator includes a bone screw clamp for receiving a first bone screw which is connected to the first bone portion and which includes a spherical portion. The fixator further includes a bone screw clamp which is operable to receive a second bone screw which is connected to the second bone portion and which has a spherical portion. The fixator also includes a connection member having a radiographic window to permit radiographic examination of the bone fracture, as well as a cantilever member operable to secure the circle portions of the first and second bone screw clamps to the connection member.

20 Claims, 3 Drawing Sheets

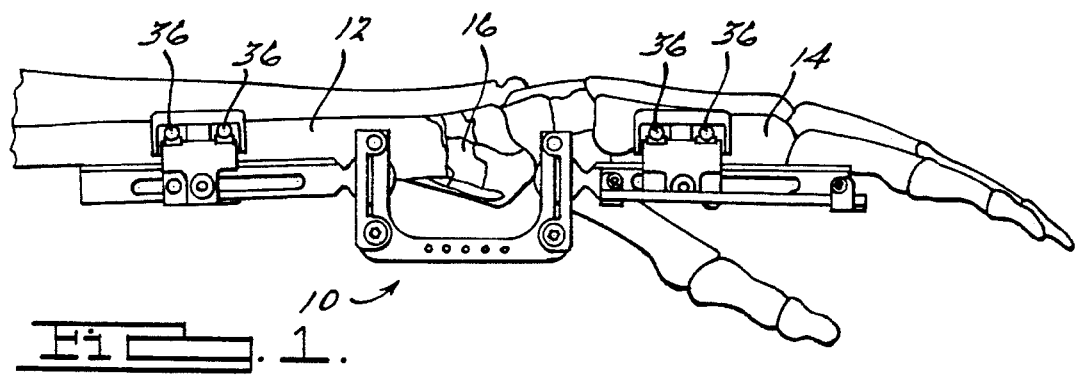
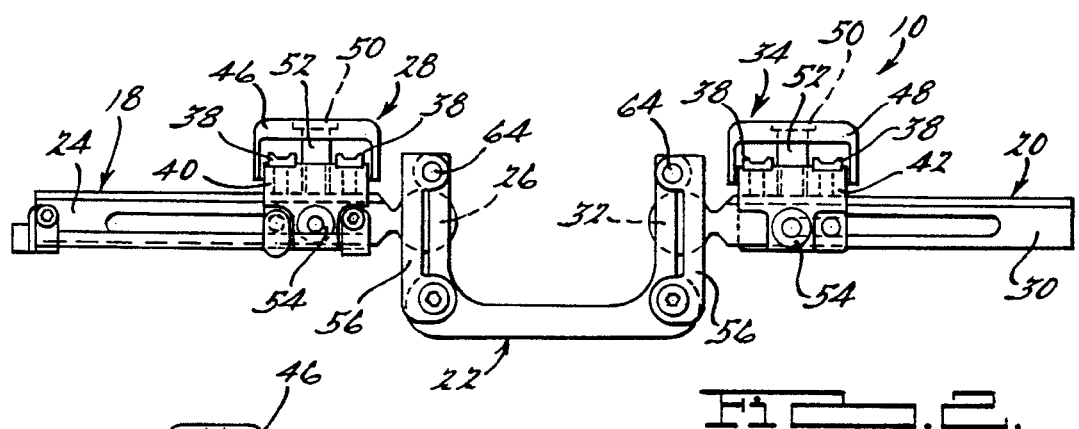
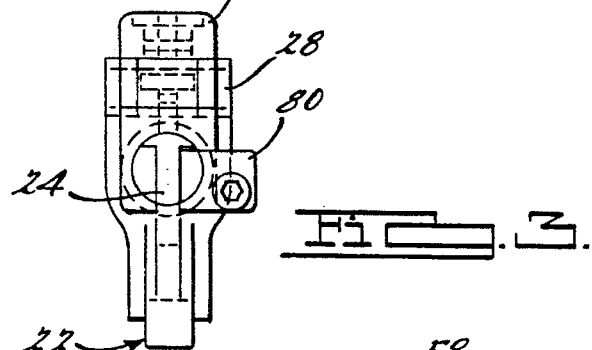
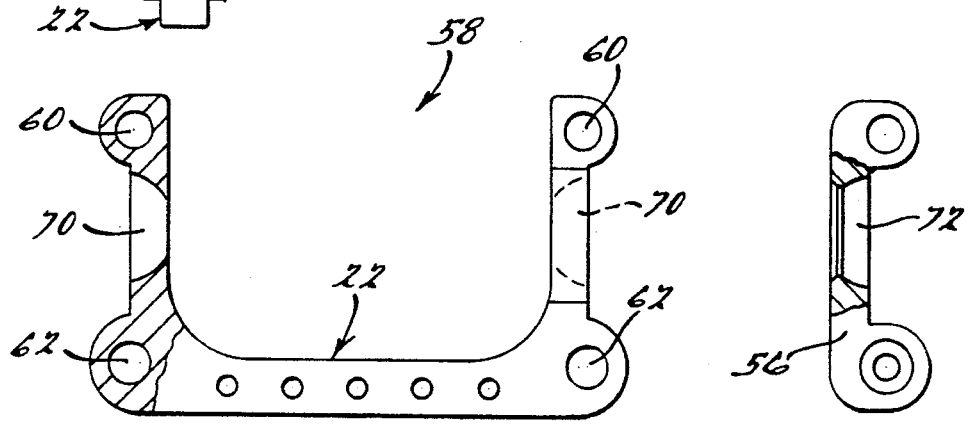

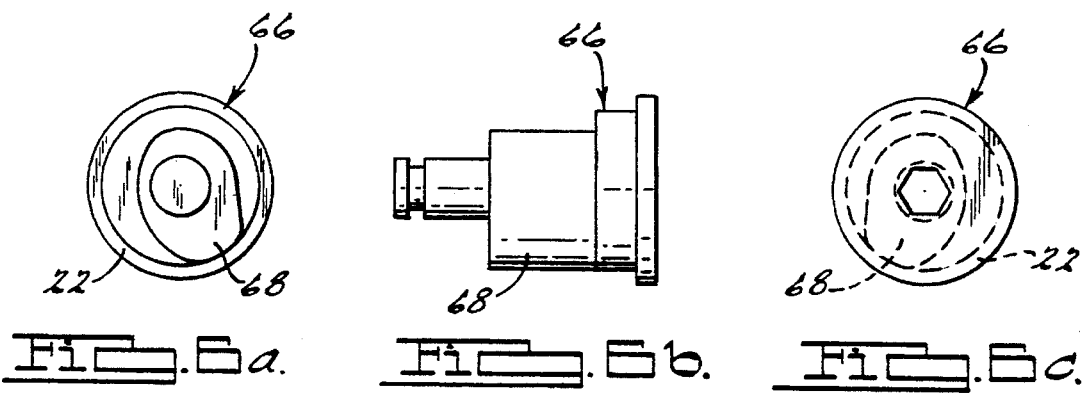
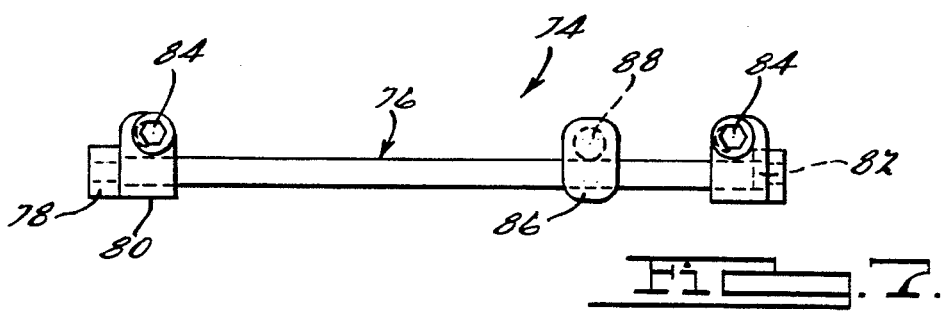
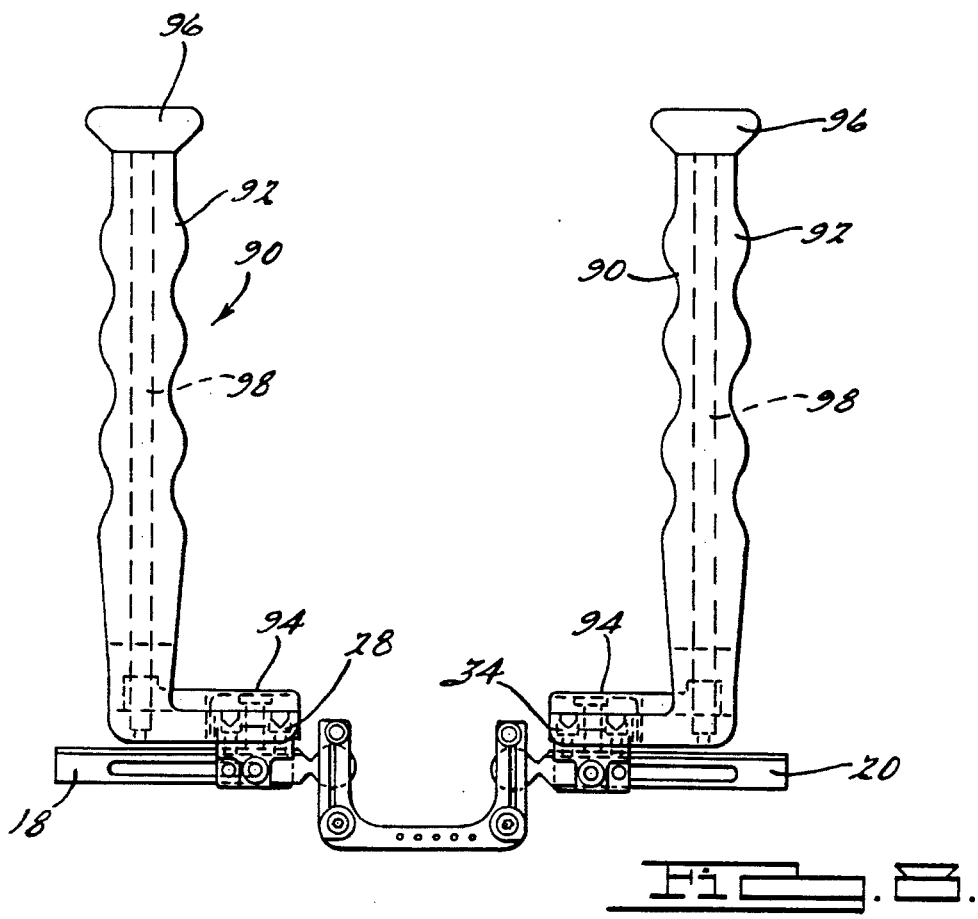

METHOD AND APPARATUS FOR EXTERNAL FIXATION OF SMALL BONES

BACKGROUND OF THE INVENTION

1. Field of the Invention

The present invention relates generally to an orthopedic surgical procedure, and more particularly to a method and apparatus for external fixation of small bones.

2. Description of the Related Art

In various orthopedic surgical procedures, it is often necessary to secure two or more portions of bone in a relatively fixed relationship to each other. This need is often a result of a fracture which has occurred to the bone. To ensure that the bone can properly regenerate and fuse the fractures of the bone, it is important that the various bone portions be fixed at the desired position during bone regeneration.

The various external fixators are known for the fixation of small bones during a surgical procedure. For example, one particular type of fixator sold by Orthofix S.r.l. for small bones has two bone screw clamps with a barbell-shaped connector disposed between the bone screw clamps. The barbell-shaped connector is captured by a bushing and an apertured nut which is able to screw on to the end of each of the bone screw clamps. A cam is used to force the bushing in a direction so as to cause the bushing to force the rounded end of the barbell-shaped connector against the apertured nut to secure the position of the barbell-shaped connector with respect to the bone screw clamp. The bone screw clamp includes a body which is able to slide on the arm of the bone screw clamp and has a cover with a plurality of circular grooves disposed thereon. The circular grooves are used to receive a plurality of bone screws.

While fixators of the type described above are effective in fixating bones, they nevertheless can be the subject of certain improvements. For example, it would be useful to have a mechanism by which the member connecting the two bone screw clamps can be more rigidly secured than simply by a cam operating directly against a bushing. In addition, the barbell-shaped nature of the interconnection between the bone screw clamps limits the ability of the physician to view the fracture in that the barbell connector is not radiolucent. In addition, unless the cylindrical grooves in the bone screw clamps are made to exactly match the shape of the bone screws, the bone screw clamps would only provide two point fixation of the bone screws.

SUMMARY OF THE PRESENT INVENTION

According to one aspect of the present invention, the invention relates to a fixator operable for securing two portions of bone in a fixed relationship to each other, with the first bone portion having a first bone screw attached thereto while the second bone portion has a second bone screw attached thereto. The fixator includes first means for receiving the first bone screw which has a spherical portion. In addition, the fixator includes a second means for receiving a second bone screw which also has a spherical portion. The fixator further includes means for securing the first means for receiving a first bone screw to the second means for receiving the second bone screw. The means for securing include a connection member which is operable to form a radiographic window to permit radiographic examination of the fracture, as well as a cantilever member operable to secure the spherical portion of said first means for receiving the first bone screw to the connection member.

An advantage of the present invention is to provide a method and apparatus for fixation of small bones that more rigidly secures movement of a bone screw clamp with respect to the body of the fixator.

Another advantage of the present invention is to provide a method and apparatus for fixation of small bones which permits radiographic examination of the fracture site.

Another advantage of the present invention is to provide a method and apparatus for fixation of small bones in which the bone screw clamp is able to provide three point fixation of bone screws.

A related advantage of the present invention is to provide a method and apparatus for securing small bones in which the bone screw clamp is positioned with respect to the body of the fixator by means of a cantilever member.

Another advantage of the present invention is the provision of a method and apparatus for the fixation of small bones having a cam which generates a relatively large amount of locking force to secure the angular position of the bone screw clamp.

Additional advantages and features of the present invention will become apparent from the following description and appended claims, taken in conjunction with the accompanying drawings.

BRIEF DESCRIPTION OF THE DRAWINGS

FIG. 1 is an illustration of the apparatus for fixation of small bones in operative association with a wrist joint according to the teachings of the preferred embodiment of the present invention;

FIG. 2 is an elevational view of the apparatus for fixation of small bones shown in FIG. 1 according to the teachings of the preferred embodiment of the present invention;

FIG. 3 is a side elevational view of the apparatus for fixation of small bones shown in FIG. 2 according to the teachings of the preferred embodiment of the present invention;

FIG. 4 is an elevational view of the cantilever member of the apparatus for fixation of small bones shown in FIG. 2 according to the teachings of the preferred embodiment of the present invention;

FIG. 5 is an elevational view of the locking member used in association with the apparatus for fixation of small bones shown in FIG. 2 according to the teachings of the preferred embodiment of the present invention;

FIG. 6(a)–(c) are elevational views of the locking cam used in conjunction with the apparatus for fixation of small bones shown in FIG. 2 according to the teachings of the preferred embodiment of the present invention;

FIG. 7 is an elevational view of the compression/distraction mechanism of the apparatus for fixation of small bones shown in FIG. 2 according to the teachings of the preferred embodiment of the present invention;

FIG. 8 is an illustration of the apparatus for fixation of small bones shown in operative association with a set of forceps used to locate the apparatus according to the teachings of the preferred embodiment of the present invention;

DETAILED DESCRIPTION OF THE PREFERRED EMBODIMENT

Figure 9A:
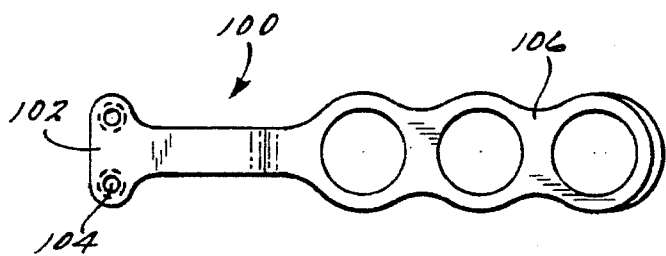
FIGS. 9(a)–9(b) are illustrations of a drill guide used to locate holes for receiving bone pins which are used with the apparatus for fixation of bones according to the teachings of the preferred embodiment of the present invention.

The following description of the preferred embodiment of the present invention is merely exemplary in nature and is in no way intended to limit the invention or its application or uses.

Referring to FIG. 1, an apparatus 10 for fixation of small bone portions 12 and 14 is shown. In particular, the apparatus 10 is illustrated as being used to secure a bone fracture 16 which is located in close proximity to the wrist joint. The apparatus 10 is used to secure the bone portions 12 and 14 in a fixed relationship so as to permit the fractured portions to fuse properly. While the apparatus 10 is shown in conjunction with a wrist joint, it will be appreciated that the apparatus 10 may be used with other joints as well.

The construction of the apparatus 10 will now be described with reference to FIGS. 2 and 3. The apparatus 10 includes a first clamp support arm 18 and a second clamp support arm 20. The first and second clamp support arms 18 and 20 are connected to each other by means of a connection member 22 as will be more fully discussed below. The first clamp support arm 18 includes an extension portion 24 and a spherical portion 26. The extension portion 24 of the first clamp support arm 18 is used to allow a first bone screw clamp 28 to slide thereon as described below. The spherical projection 26 extends from the extension portion 24 and is used to engage the connection member 22. In a similar fashion, the second clamp support arm 20 also includes an extension portion 30 and a spherical portion 32. As with the first clamp support arm 18, the extension portion 30 is used to allow a second bone screw clamp 34 to slide thereon, while the spherical projection 32 extends from the extension portion 30 and serves to allow engagement with the connection member 22.

As discussed above, the first and second bone screw support clamps 28 and 34 are operable to slide on the first extension portion 24 and the second extension portion 30, respectively, and are operable to support a plurality of bone screws 36 after they have been secured to bone. To secure the bone screws 36 to the bone screw clamps 28 and 34, the bone screw clamps 28 and 34 include a plurality of bone screw rests 38. The bone screw rests 38 contain a V-shaped groove which is operable to engage the sides of the bone screws 36. The bone screw rests 38 are secured to the bodies 40 and 42 of the bone screw clamps 28 and 34 by staking a projection extending from the bottom of the bone screw rests 38. However, the staking operation is performed such as to allow approximately 0.002" difference between the length of the projection and the depth of the bore receiving the projection in the bodies 40 and 42 so as to allow limited movement of the bone screw rests 38. This limited movement of the bone screw rests 38 allows the bone screw rests 38 to center on the bone screws 36 and therefore not cause the bone screws 36 to otherwise stress the bone when the bone screws are not precisely aligned with the groove of the bone screw rests 38.

The bone screw clamps 28 and 34 further each include cover members 46 and 48 which are able to be inserted over the bone screws 36 when the bone screws 36 are located in the bone screw rests 38. The cover members 46 and 48 each include an aperture 50 which allows a threaded fastener 52 to pass through the cover members 46 and 48 and into a threaded aperture of the bodies 40 and 42 of the bone screw clamps 28 and 34.

To secure the position of the bone screw clamps 28 and 34 on the extension portions 24 and 30 of the first and second clamp support arms 18 and 20, the apparatus further includes a plurality of locking screws 54. The locking screws 54 are operable to threadably engage the bodies 40 and 42 of the bone screw clamps 28 and 34 and extend therethrough to engage the extension portions 24 and 30 of the first and second clamp support arms 18 and 20, respectively. Accordingly, upon rotation of the locking screws 54, the locking screws 54 are able to engage the extension portions 24 and 30 of the first and second clamp support arms 18 and 20 so as to prevent longitudinal movement of the bone support clamps 28 and 34.

The connection member 22 and the cantilever member 56 will now be described with reference to FIGS. 4 and 5. The connection member 22 is generally U-shaped so as to form a radiographic window 58 through which the fracture 16 may be viewed. The connection member 22 includes a first plurality of apertures 60 as well as a second plurality of apertures 62. The first plurality of apertures 60 are operable to receive a locking pin 64 which extends through the cantilever members 62 as well as the connection member 22 so as to form a hinge between the connection member 22 and the cantilever members 62. The second plurality of apertures 62 are used to receive a locking cam 66 which also extends through the apertures of the cantilever members 56. The locking cam 66 (shown in FIG. 6) includes a non-circular camming portion 68 which engages one of the second plurality of apertures 62 at an angle which is less than the angle which would be engaged if the cross-section of the camming portion 68 were circular in cross-section. Accordingly, the approach angle of the camming portion 68 with respect to one of the second plurality of apertures 62 is reduced so as to allow less resistance to rotation when the locking cam 66 is rotated so as to secure the spherical portion of the clamp support arm 18 between the cantilever member 56 and the connection member 22. Accordingly, the locking cam 66 is able to generate greater force for securing the cantilever member 56 to the connection member 22 for a given applied torque.

The connection member 22 also has a plurality of central apertures 70 which are able to receive the spherical portions 26 and 32 of the first and second clamp support arms 18 and 20 while each of the cantilever members 56 also includes a central aperture 72 which is able to receive part of the spherical portions 26 and 32 of the first and second clamp support arms 18 and 20. Accordingly, when the locking cam 66 is rotated in such a manner so as to displace the cantilever member 56 in a direction towards the connection member 22, the spherical portions 26 and 32 of each of the clamp support arms 18 and 20 are securely engaged between the connection member 22 and the cantilever members 56.

To allow the bone screws 36 which are disposed within the first bone screw clamp 28 to be longitudinally displaced, the first clamp support member 28 further includes a compression/distraction assembly 74 as shown in FIG. 7. The compression/distraction assembly 74 includes a threaded pin 76 having a head 78 with a hex-shaped recess. The threaded pin 76 is secured to the first clamp support arm 28 by means of a first mounting member 80 and a second mounting member 82, each of which is attached by means of a threaded fastener 84. The compression/distraction assembly 74 further includes a movable member 86 which threadably engages the threaded pin 76 of the compression/distraction assembly 74. The movable member 86 includes a pin 88 which engages a recess in the body 40 of the first bone screw clamp 28. As will be appreciated by those skilled in the art, rotation of the threaded pin 76 causes the movable member 86 to be displaced with respect to the first and second mounting members 80 and 82. Because the pin 88 of the movable member 86 engages the bone screw clamp 28, the bone screw clamp 28 is also able to move upon rotation of the threaded pin 76.

It is often necessary to locate the apparatus while the joint in question is being subjected to radiation. For this reason, the apparatus 10 may also be used with a plurality of forceps 90 shown in FIG. 8. In this regard, the forceps 90 include a handle 92 which has a bone screw engaging portion and a rotatable knob 96. The rotatable knob 96 is secured to a threaded member 98 which extends to the bone screw engaging portion 94. Accordingly, by rotation of the knob 96, the bone screw engagement portion 94 can clamp the bone screws 36 in a secure manner. When the forceps 90 are used, the bone screws 36 are initially clamped by the forceps 90 and then the forceps 90 are used to manipulate the position of the apparatus 10. Once the apparatus 10 is in the proper position, the cams 66 are rotated so as to secure the spherical portions 26 and 32 of the clamp support arms 18 and 20 to the connection member 22 and the threaded fasteners 54 are rotated so as to secure the position of the bone screw clamps 28 and 34 with respect to the clamp support arms 18 and 20.

Figure 9B:
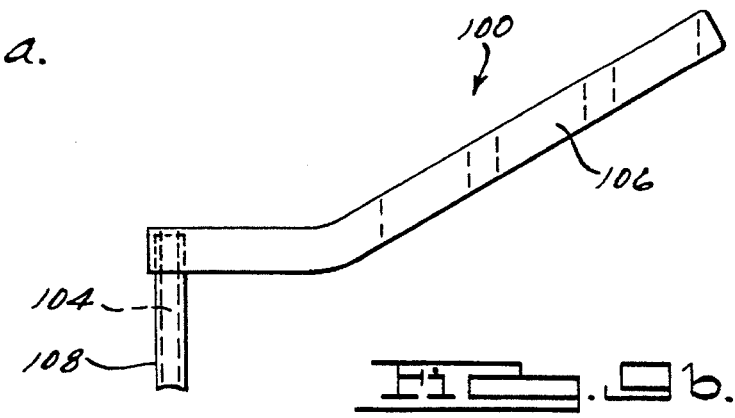

To facilitate the positioning of the bone screws 36 when using the apparatus 10, a drill guide 100 similar to that shown in FIG. 9 may be used. The drill guide 100 includes a guide portion 102 having two longitudinal bores 104 extending therethrough. The drill guide 100 also includes a handle portion 106 which may be used to position the guide portion 102. In operation, the guide portion 102 of the drill guide 100 is positioned such that the circular projections 106 of the guide portion 102 are received through a soft tissue sleeve (not shown) which engages the bone screw rests 38 of the bone screw clamps 28 and 34. A drill is then used to form a hole in the bone and then the drill and the drill guide 100 are removed. A bone screw 36 is then inserted into the soft tissue sleeve and then is secured to the bone. The soft tissue sleeve is then removed and then the bone screw is secured to the bone screw clamp 28 by rotation of the threaded fastener.

Figure 10A:
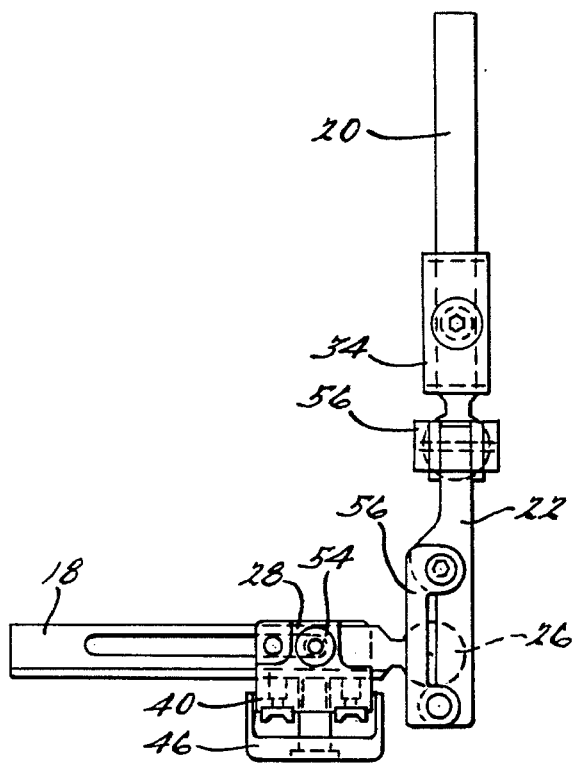
FIG. 10 is an illustration of the apparatus for fixation of small bones according to the second preferred embodiment of the present invention.
Figure 10B:
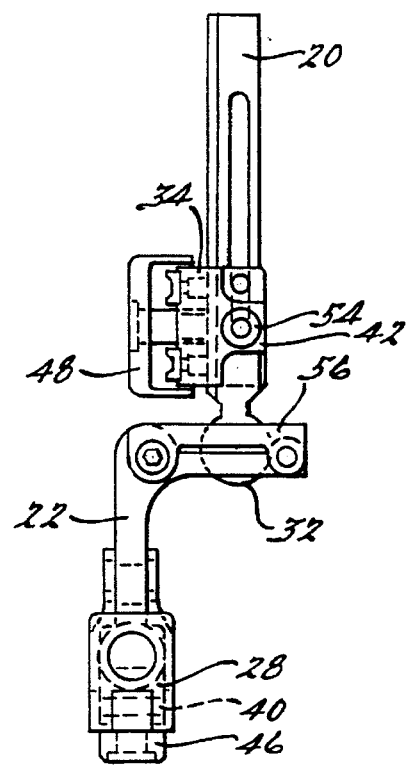

The second preferred embodiment of the present invention is shown in FIG. 10. In this embodiment, similar reference numerals will be used to identify similar components as previously described with respect to the first preferred embodiment of the present invention. As with the first preferred embodiment of the present invention, the apparatus 10 of the second embodiment of the present invention includes a first clamp support arm 18 and a second clamp support arm 20. A first bone screw clamp 28 is located on the first clamp support arm 18, while a second bone screw clamp 34 is located on the second clamp support arm 20. The first and second clamp support arms 18 and 20 are connected by a connection member 22 which is operable to locate the first clamp support arm 18 at a position which is below and at right angles to the second bone support arm 20. This allows the apparatus to be used in other forms of fixation of small bones.

In use, the apparatus 10 is initially oriented in the position where it is desired to be ultimately secured to the bone. A soft tissue sleeve (not shown), followed by the drill guide 100, is inserted into the first bone screw support clamp 28 and onto the bone screw rest 38 of the bone screw clamp 28. A drill is then used to form two holes in the bone and then the drill guide 100 is removed from the first bone screw clamp 28. Two bone screws 36 are then inserted into the soft tissue sleeve and are rotated so as to securely engage the bone. The soft tissue sleeve is then removed from the bone screw clamp 28 and then the cover member 46 is secured to the body 40 of the bone screw clamp 28. This process is then repeated with respect to the bone screws 36 which are inserted into the second bone screw clamp 34.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention.

What is claimed is:

1. An apparatus for securing a first bone portion in a fixed relationship to a second bone portion, the apparatus comprising:

a first bone screw connected to the first bone portion;

a second bone screw connected to the second bone portion;

means for receiving said first bone screw, said means for receiving said first bone screw having a spherical portion;

means for receiving said second bone screw, said means for receiving said second bone screw having a spherical portion; and means for securing said means for receiving said first bone screw to said means for receiving said second bone screw, said means for securing being operative to at least partially define a radiographic window to permit radiographic examination of the fixed relationship of the first and second bone portions in a direction substantially parallel to said first bone screw, said radiographic window extending directly between said spherical portion of said means for receiving said first bone screw and said spherical portion for said means for receiving said second bone screw.

2. The apparatus for securing a first bone portion in a fixed relationship to a second bone portion of claim 1, wherein said means for securing said means for receiving said first bone screw to said means for receiving said second bone screw includes an intermediate portion having a longitudinal axis spaced apart from a line passing through said spherical portion of said means for receiving said first bone screw and said spherical portion of said means for receiving said second bone screw.

3. The apparatus for securing a first bone portion in a fixed relationship to a second bone portion of claim 2, further comprising a cantilevered member operable to secure the spherical portion of said means for receiving said first bone screw to said means for securing said means for receiving said first bone screw to said means for receiving said second bone screw.

4. The apparatus for securing a first bone portion in a fixed relationship to a second bone portion of claim 3, wherein said means for securing said means for receiving said first bone screw to said means for receiving said second bone screw comprises a generally U-shaped connecting member, and further wherein said cantilevered member includes a first end pivotally interconnected with said connecting member for selective rotation through a camming member.

5. The apparatus for securing a first bone portion in a fixed relationship to a second bone portion of claim 1, wherein said means for receiving said first bone screw includes means for longitudinally displacing said first bone screw relative to said spherical portion of said means for receiving said first bone screw.

6. The apparatus for securing a first bone portion in a fixed relationship to a second bone portion of claim 1, wherein said means for receiving said first bone screw includes means for establishing three point contact with said first bone screw.

7. The apparatus for securing a first bone portion in a fixed relationship to a second bone portion of claim 1, wherein said means for receiving said first bone screw includes a base portion and a cover portion, said base portion and said cover portion cooperatively defining a channel adapted to receive said first bone screw, one of said base portion and said cover portion including a substantially V-shaped groove for directly engaging said first bone screw in two point contact and the other of said base portion and said cover portion engaging said first bone screw at a third point of contact.

8. An apparatus for securing a first bone portion in a fixed relationship to a second bone portion by a first bone screw connected to the first bone portion and a second bone screw connected to the second bone portion, the apparatus comprising:

a first clamping member for receiving the first bone screw, said first clamping member including a spherical portion;

a second clamping member for receiving the second bone screw, said second clamping member including a spherical portion; and a connecting member for securing said first clamping member to said second clamping member, said connecting member including an intermediate portion having a longitudinal axis spaced apart from a line passing through said spherical portion of said first clamping member and said spherical portion of said second clamping member in a direction substantially normal to the first bone screw.

9. The apparatus for securing a first bone portion in a fixed relationship to a second bone portion of claim 8, further comprising a cantilevered member operable to secure said spherical portion of first clamping member to said connecting member.

10. The apparatus for securing a first bone portion in a fixed relationship to a second bone portion of claim 9, wherein said connecting member further includes a transversely extending portion disposed generally perpendicular to said intermediate portion having an aperture, and further wherein said cantilevered member includes an aperture, said spherical portion of said first clamping member being centered between said cantilevered member and said transversely extending portion such that said spherical portion of said first clamping member partially extends into said aperture of said transversely extending portion and partially extends into said aperture of said cantilevered member.

11. The apparatus for securing a first bone portion in a fixed relationship to a second bone portion of claim 10, further comprising a camming member for selectively preventing relative rotation between said spherical portion of said first clamping member and said cantilevered member.

12. The apparatus for securing a first bone portion in a fixed relationship to a second bone portion of claim 8, wherein said first clamping member includes a longitudinally displaceable portion for receiving the first bone screw.

13. The apparatus for securing a first bone portion in a fixed relationship to a second bone portion of claim 12, further comprising a mechanism for incrementally advancing said longitudinally displaceable portion relative to the spherical portion of said first clamping member.

14. The apparatus for securing a first bone portion in a fixed relationship to a second bone portion of claim 8, wherein said first clamping member includes a base portion and a cover portion, and further wherein one of said base portion and said cover portion includes a substantially V-shaped groove for directly engaging the first bone screw in two point contact and the other of said base portion and said cover engages said first bone screw at a third point of contact.

15. The apparatus for securing a first bone portion in a fixed relationship to a second bone portion of claim 8, wherein said connecting member is generally U-shaped having a pair of transversely extending portions disposed generally perpendicular to said intermediate portion.

16. An apparatus for securing a first bone portion in a fixed relationship to a second bone portion by a first bone screw connected to the first bone portion and a second bone screw connected to the second bone portion, the apparatus comprising:

a first clamping member for receiving the first bone screw;

a second clamping member for receiving the second bone screw; and a connecting member for securing said first clamping member to said second clamping member, said connecting member having a substantially U-shaped configuration for at least partially defining a radiographic window to permit radiographic examination of the fixed relationship of the first and second bone portions.

17. The apparatus for securing a first bone portion in a fixed relationship to a second bone portion of claim 16, further comprising a cantilevered member operable to secure said first clamping member to said connecting member.

18. The apparatus for securing a first bone portion in a fixed relationship to a second bone portion of claim 17, wherein said connecting member is unitarily formed and includes an intermediate portion and a transversely extending portion disposed generally perpendicular to said intermediate portion.

19. The apparatus for securing a first bone portion in a fixed relationship to a second bone portion of claim 18, wherein said first clamping member includes a spherical portion, and further wherein transversely extending portion includes an aperture and said cantilevered member includes an aperture, said spherical portion of said first clamping member being centered between said cantilevered member and said transversely extending portion such that said spherical portion of said first clamping member partially extends into said aperture of said transversely extending portion and partially extends into said aperture of said cantilevered member.

20. The apparatus for securing a first bone portion in a fixed relationship to a second bone portion of claim 19, further comprising a camming member for selectively preventing relative rotation between said spherical portion of said first clamping member and said cantilevered member.

* * * * *